United States Patent
Devlin et al.

(10) Patent No.: US 6,387,841 B1
(45) Date of Patent: May 14, 2002

(54) POLYOXOMETALLATE SUPPORTED CATALYSTS

(75) Inventors: Anna. Marie Devlin, Hatfield, PA (US); Anthony Frank Volpe, Jr., Santa Clara, CA (US)

(73) Assignee: Rohm and Haas Company, Philadelphia, PA (US)

(*) Notice: Subject to any disclaimer, the term of this patent is extended or adjusted under 35 U.S.C. 154(b) by 0 days.

(21) Appl. No.: 09/626,640

(22) Filed: Jul. 27, 2000

Related U.S. Application Data
(60) Provisional application No. 60/150,309, filed on Aug. 23, 1999.

(51) Int. Cl.[7] .................. B01J 27/14; B01J 23/00; B01J 23/72; B01J 23/16
(52) U.S. Cl. .................. 502/208; 502/209; 502/210; 502/211; 502/212; 502/213; 502/302; 502/303; 502/305; 502/308; 502/311; 502/312; 502/313; 502/319; 502/325; 502/326; 502/331; 502/344; 502/345; 502/349; 502/353
(58) Field of Search .................. 502/208–213, 502/305–355

(56) References Cited

U.S. PATENT DOCUMENTS

| | | | | |
|---|---|---|---|---|
| 4,634,502 A | * | 1/1987 | Callahan et al. | 204/23 |
| 4,898,989 A | | 2/1990 | Ellis, Jr. et al. | 568/399 |
| 5,380,933 A | * | 1/1995 | Ushikubo et al. | 562/549 |
| 5,705,685 A | | 1/1998 | Lyons et al. | 562/549 |
| 6,043,184 A | * | 3/2000 | Karmakar et al. | 502/208 |
| 6,060,419 A | * | 5/2000 | Wijesekera et al. | 502/208 |

FOREIGN PATENT DOCUMENTS

| | | |
|---|---|---|
| EP | 0 301 723 | 2/1989 |
| EP | 0 471 853 | 2/1992 |
| WO | WO 95/13869 | 5/1995 |
| WO | WO 00/09262 | 2/2000 |

OTHER PUBLICATIONS

Herron, et al., "Molecular Precursors to Vanadyl Pyrophosphate and Vanadyl Phosphite", J. Am. Chem. Soc. 1997, 119, 7149–7150. Jan. 1997.

* cited by examiner

*Primary Examiner*—Mark L. Bell
*Assistant Examiner*—Patricia L. Hailey
(74) *Attorney, Agent, or Firm*—Alan Holler

(57) ABSTRACT

Disclosed are catalysts situated on a polyoxometallate support. Also disclosed are methods of preparing these catalysts and processes for the conversion of alkanes to unsaturated organic compounds using these catalysts.

13 Claims, 1 Drawing Sheet

POLYOXOMETALLATE SUPPORTED CATALYSTS

This application claims benefit to Provisional Application 60/150,309 filed Aug. 28, 1999.

BACKGROUND OF THE INVENTION

This invention relates generally to improved catalysts for a variety of chemical processes. In particular, this invention relates to catalysts supported on polyoxometallate salts.

In general, catalysts are well known for a variety of chemical processes. For example, certain oxidation catalysts are particularly useful for the preparation of products, such as alcohols, carboxylic acids, alkenes, alkynes, and the like, from alkanes. One class of catalysts, heteropolyacids, are known to be supported, e.g., on polyoxometallate salts, to improve their performance and because of their inherent instability. For example, US 5,705,685 (Lyons et al.) discloses heteropolyacids supported on polyoxometallate salts for the oxidation of alkanes to unsaturated carboxylic acids. No other catalysts are disclosed in Lyons et al.

Although many catalysts, such as mixed metal oxides are often supported, others, such as vanadium phosphorus compounds, are typically not supported because these catalysts perform poorly when supported and are stable by themselves. However, since reaction takes place on the surface of most heterogeneous catalysts, there has been a growing interest in supporting catalysts in order to maximize the catalyst surface, and thus improve performance. Such supports include silica, zirconia, alumina, titania, diatomaceous earth, and the like. However, such supports often produce catalysts with low selectivities.

Herron et al., Molecular Precursors to Vanadyl Pyrophosphate and Vanadyl Phosphite, *Journal of the American Chemical Society*, vol. 119, 7149–7150 (1997), disclose the need for supported vanadium phosphorus catalysts, particularly for the production of maleic anhydride. Traditional methods of catalyst preparation have made it difficult to prepare the desired high surface area supported catalysts having well defined stoichiometry and phase. Herron et al disclose specific molecular clusters of vanadyl catalysts as a method of supporting such catalysts on silica. However, such molecular clusters are not easily adaptable to supporting other types of catalysts. Herron et al. do not disclose supporting such molecular clusters on any other supports.

Thus, there is a continuing need for supported catalysts having a maximized surface area, a controlled surface area and high selectivities.

SUMMARY OF THE INVENTION

It has been surprisingly found that polyoxometallate salts can be used to support a variety of catalysts.

In one aspect, the present invention is directed to a catalyst composition including a catalyst situated on a polyoxometallate support; wherein the polyoxometallate support has the formula $$Q_aH_{(e-az)}(X_kM_{m-x}M^1_xM^2_nO_y)^{-e} \quad (I)$$

wherein Q, is a cation selected from potassium, rubidium, cesium, magnesium, calcium, strontium, barium, transition metal, actinide metal, lanthanide metal, metal oxy ion, ammonium, tetraalkylammonium, pyridinium, quinolinium, protonated aromatic amines, protonated aliphatic amines or mixtures thereof; X is an element selected from Groups 3–16 elements; M=molybdenum, tungsten or a combination thereof, M$^1$=vanadium; M$^2$ is a transition metal different from M and M$^1$; z=the charge on Q; k=1 to 5; m=5 to 20; n=0 to 3; x=0 to 6; y=18 to 62; and e is the charge of the polyoxometallate anion; and provided that the catalyst is not a heteropolyacid.

In a second aspect, the present invention is also directed to a process for preparing a catalyst composition including a catalyst situated on a polyoxometallate support; wherein the polyoxometallate support has the formula $$Q_aH_{(e-az)}(X_kM_{m-x}M^1_xM^2_nO_y)^{-e} \quad (1)$$

wherein Q is a cation selected from potassium, rubidium, cesium, magnesium, calcium, strontium, barium, transition metal, actinide metal, lanthanide metal, metal oxy ion, ammonium, tetraalkylammonium, pyridinium, quinolinium, protonated aromatic amines, protonated aliphatic amines or mixtures thereof; X is an element selected from Groups 3–16; M is as defined above; M$^1$=vanadium; M$^2$ is a transition metal different from M and M$^1$; z=the charge on Q; k=1 to 5; m=5 to 20; n=0 to 3; x=0 to 6; y=18 to 62; and e is the charge of the polyoxometallate anion; including the step of admixing the catalyst with the polyoxometallate support; provided that the catalyst is not a heteropolyacid.

In a third aspect, the present invention is directed to a process for preparing unsaturated organic compounds including the steps of contacting an alkane with an oxidizing agent and a catalyst composition including one or more mixed metal oxides, vanadium phosphorus compounds or mixtures thereof situated on a polyoxometallate support; wherein the mixed metal oxide has the formula $$A_{a'}M^3_{m'}L_{l'}Z_{z'}O_o \quad (II)$$

wherein A is selected from molybdenum, tungsten, iron, niobium, tantalum, zirconium, ruthenium, and mixtures thereof; M$_3$ is selected from vanadium, cerium, chromium, and mixtures thereof; L is selected from tellurium, bismuth, antimony, selenium, and mixtures thereof; Z is selected from niobium, tantalum, tungsten, titanium, aluminum, zirconium, chromium, manganese, iron, ruthenium, cobalt, rhenium, nickel, palladium, platinum, antimony, bismuth, boron, indium, cerium, and mixtures thereof; a'=0.25 to 0.98; m'=0.003 to 0.5; l=0.003 to 0.5; z'=0.003 to 0.5; o is dependent on the oxidation state of the other elements; and wherein the polyoxometallate support has the formula $$Q_aH_{(e-az)}(X_kM_{m-x}M^1_xM^2_nO_y)^{-e} \quad (II)$$

wherein Q is a cation selected from potassium, rubidium, cesium, magnesium, calcium, strontium, barium, transition metal, actinide metal, lanthanide metal, metal oxy ion, ammonium, tetraalkylammonium, pyridinium, quinolinium, protonated aromatic amines, protonated aliphatic amines or mixtures thereof; X is an element selected from Groups 3–16 elements; M=molybdenum, tungsten or a combination thereof; M$^1$=vanadium; M$^2$ is a transition metal different from M and M$^1$; z= the charge on Q; k=1 to 5; m=5 to 20; n=0 to 3; x=0 to 6; y=18 to 62; and e is the charge of the polyoxometallate anion.

In a fourth aspect, the present invention is directed to a process for preparing a mixed metal oxide catalyst of the formula $$A_{a'}M^3_{m'}L_{l'}Z_{z'}O_o \quad (II)$$

wherein A is selected from molybdenum, tungsten, iron, niobium, tantalum, zirconium, ruthenium, and mixtures thereof; M³ is selected from vanadium, cerium, chromium, and mixtures thereof; L is selected from tellurium, bismuth, antimony, selenium, and mixtures thereof; Z is selected from niobium, tantalum, tungsten, titanium, aluminum, zirconium, chromium, manganese, iron, ruthenium, cobalt, rhenium, nickel, palladium, platinum, antimony, bismuth, boron, indium, cerium, and mixtures thereof; a'=0.25 to 0.98; m'=0.003 to 0.5; l=0.003 to 0.5; z'=0.003 to 0.5; o is dependent on the oxidation state of the other elements; including the step of heating a mixed metal oxide molecular precursor at a temperature of at least 600° C. for a period of time sufficient to convert the precursor to the mixed metal oxide.

DETAILED DESCRIPTION OF THE INVENTION

Figure 1:
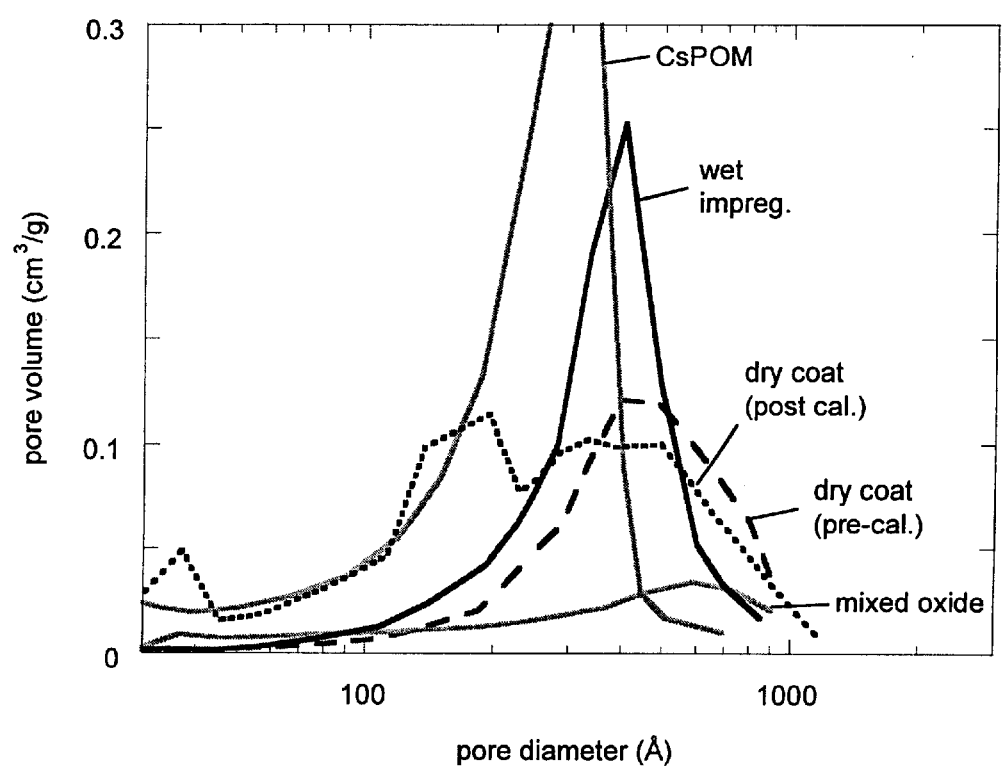
FIG. 1 shows a plot of pore volume versus pore diameter for mixed metal oxide catalysts supported on a cesium polyoxometallate prepared by various methods.

As used throughout the specification, the following terms shall have the following meanings, unless the context clearly indicates otherwise.

The term "alkane" includes linear, branched and cyclic alkanes. Likewise, the term "alkene" includes linear, branched and cyclic alkenes. All elements are referred to using the nomenclature recommended by the International Union of Pure and Applied Chemistry ("IUPAC"). As used herein, the term "transition metal" refers to an element of Groups 3–12 and includes the lanthanide and actinide series.

All ratios and amounts are by weight, unless otherwise noted. All numerical ranges are inclusive, unless otherwise noted. The following abbreviations are used throughout the specification: C=Centigrade; AA=acrylic acid; POM= polyoxometallate; HPA=heteropolyacid; MMO=mixed metal oxide; g=gram; mol=mole; m=meter; Å=angstrom; and ml=milliliter.

The polyoxometallate salts of the present invention consist of a polyhedral cage structure or framework bearing a negative charge (e.g., $[PW_{12}O_{40}]^{-3}$) which is balanced by cations that are external to the cage. In a polyoxometallate salt, none of the cations are protons. Typical cations in polyoxometallate salts include metals such as an alkali metal, potassium, sodium, cesium or lithium, as in $K_3PW_{12}O_{40}$, or ammonium, as in $(NH_4)_3PW_{12}O_{40}$. Polyoxoanion describes the anionic cage-like portion of the compound, e.g. $[PW_{12}O_{40}]^{-3}$.

Polyoxometallate salts are cage-like structures with a primary, generally centrally located atom(s) surrounded by a cage framework, which framework contains a plurality of metal atoms, the same or different, bonded to oxygen atoms. The central element of polyoxometallates is different from metal atoms of the framework and is sometimes referred to as the "hetero" element or atom; the condensed coordination elements are referred to as the "framework" elements or metals, and are ordinarily transition metals. The majority of polyoxometallates have a centrally located heteroatom ("X") usually bonded in a tetrahedral fashion through four oxygen atoms to the "framework" metals ("M"). The framework metals, in turn, (i) are usually bonded to the central atom in an octahedral fashion through oxygens ("O"), and (ii) are bonded to four other framework metals through oxygen atoms and (iii) have a sixth non-bridging oxygen atom known as the "terminal oxygen" atom. This is illustrated by Formula (III).

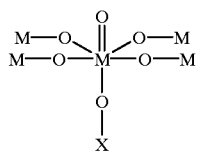

(III)

The principal framework metal, M, is any that has an appropriate cation radius and is a good oxygen pπ-electron acceptor. Typically, the framework metal is selected from molybdenum, tungsten, vanadium, niobium or tantalum. It is preferred that the framework metal is molybdenum, tungsten or vanadium.

Polyoxometallates are known to exist in a variety of structures including the Keggin, Dawson and Anderson structures. These different structures correspond to the specific geometry of particular polyoxometallate compositions and vary according to the coordination chemistry and atomic radii of the metals present. Any of these structures, or mixtures thereof, are suitable for use in the present invention.

Framework-substitutedpolyoxometallates are also useful in the present invention. These compounds are polyoxometallates where certain framework atoms M (and the oxygen atoms doubly bonded to them) are replaced with transition metals. The substitution may, for example, be monosubstitution, random- or regio-disubstitution, random- or regio-trisubstitution, or higher substitutions, all of which produce effective compositions for use as the polyoxometallate support in the present invention. The polyoxometallates may be further promoted by a variety of means described below. The present invention encompasses unsubstituted polyoxometallates.

The polyoxometallates useful as supports in the present invention are typically water insoluble and are those of the formula $$Q_aH_{(e-az)}(X_kM_{m-x}M_{1x}M^2_nO_y)^{-e} \qquad (II)$$

wherein Q is a cation selected from potassium, rubidium, cesium, magnesium, calcium, strontium, barium, transition metal, actinide metal, lanthanide metal, metal oxy ion, ammonium, tetraalkylammonium,pyridinium, quinolinium, protonated aromatic amines, protonated aliphatic amines or mixtures thereof, X is an element selected from Groups 3–16; M, the first framework metal, is molybdenum, tungsten or a combination thereof; $M^1$, the second framework metal, is substituted for the first framework metal and is vanadium; $M^2$, the third framework metal, is different from M and $M^1$ and is independently transition metal; z=the charge on Q; k=1 to 5; m=5 to 20; n=0 to 3; x=0 to 6; y=18 to 62; and e' is the charge of the polyoxometallate anion. Suitable transition metals useful for Q include, but are not limited to: vanadium, chromium, lanthanum, manganese, iron, cobalt, ruthenium, copper and the like. Suitable metal oxy ions useful for Q include, but are not limited to: oxy ions of vanadium, oxy ions of chromium, oxy ions of uranium, and the like. It is preferred that Q is potassium, rubidium, cesium, magnesium, calcium, strontium, barium, lanthanum, ammonium, tetraalkylammonium,pyridinium, quinolinium, protonated aromatic amines, protonated aliphatic amines, or mixtures thereof, and more preferably cesium. Suitable transition elements for X include, but are not limited to: phosphorus, silicon, gallium, aluminum, arsenic, germanium, boron, cobalt, cerium, praseodymium, uranium, thorium or mixtures thereof. Suitable transition elements for $M_2$ include, but are not limited to: titanium, zirconium, hafnium, vanadium, niobium, tantalum, chromium, molybdenum, tungsten, manganese, rhenium, iron, cobalt, nickel, ruthenium, rhodium, palladium, osmium, iridium, platinum, copper, zinc or combinations thereof. When M is molybdenum and the compound is a Keggin ion, it is preferred that x=0 to 3. When M is tungsten and the compound is a Keggin ion, it is preferred that x=0 to 6. When "az" equals "e", there are no protons present in the polyoxometallate support, which is preferred.

Suitable polyoxometallate supports useful in the present invention include wide pore salts, for example wide pore cesium salts of the various substituted polyoxometallates described in U.S. Ser. No. 08/565,206, herein incorporated by reference to the extent it teaches the preparation of such salts. It is preferred that the polyoxometallate support is $Cs_{3+x}(PM_{12-x}V_xO_{40})$, where x=0 to 3 and M=molybdenum or tungsten. Suitable preferred polyoxometallate supports include $Cs_3(PMo_{12}O_{40})$, $Cs_4(PMo_{11}VO_{40})$, $Cs_5(PMo_{10}V_2O_{40})$, $Cs_6(PMo_9V_3O_{40})$, $Cs_4(PW_{11}VO_{40})$, $Cs_5(PW_{10}V_2O_{40})$, $Cs_6(PW_9V_3O_{40})$, or combinations thereof. It is more preferred that the polyoxometallate support is $Cs_3(PMo_{12}O_{40})$, $Cs_3(PW_{12}O_{40})$ or combinations thereof.

An advantage of the polyoxometallate supports of the present invention is that the pore size of the supports can be controlled. The polyoxometallate supports of the present invention may have large (i.e. wide) or small pores or a mixture of pore sizes. Thus, the polyoxometallate supports of the present invention may be chosen such that their pore size and pore size distribution is optimized for the particular catalyst to be supported.

When polyoxometallates having large pores are used in the present invention, the polyoxometallate support preferably has pore volumes in the range from 0.01 to 0.25 ml/g and a pore size distribution in which more than approximately 60% of the pore volume is due to pores having a median pore radius of greater than or equal to approximately 75 Å, preferably greater than or equal to approximately 100 Å, more preferably greater than or equal to approximately 150 Å, still more preferably greater than or equal to approximately 200 Å. More preferably, the support has pore volumes in the range from 0.05 to 0.25 ml/g and a pore size distribution in which more than approximately 60% of the pore volume is due to pores having a median pore radius of greater than or equal to approximately 75 Å. In a preferred embodiment, the support material has pore volumes in the range from 0.01 to 0.25 ml/g and a pore size distribution in which more than approximately 80% of the pore volume is due to pores having a median pore radius of greater than or equal to approximately 200 Å; more preferably, the support material has pore volumes greater than 0.15 ml/g and a pore size distribution in which more than approximately 80% of the pore volume is due to pores having a median pore radius of greater than or equal to approximately 200 Å. In a more preferred embodiment, the pores in the support have pore radii of greater than 75 Å and pore volumes greater than 0.05 ml/g; more preferably, the pore radii are greater than 100 Å, and independently, the pore volumes are greater than 0.1 ml/g. It has been found that supports with pore volumes greater than 0.02 ml/g result in catalysts with superior catalytic performance, provided the pores are wide (i.e., radii greater than approximately 75 Å). These polyoxometallates may be further modified by pretreatment with water, such as steam, washing with various solvents, and by formation in the presence of vanadyl acetylacetonate or $VOSO_4$. Such supports may also be ground to modify pore sizes.

The polyoxometallate salt used in the present invention may contain second framework metals which have been substituted into the framework thereof, replacing an equivalent number of the first framework metals. Such substituting metals include, but are not limited to: titanium, zirconium, hafnium, vanadium, niobium, tantalum, chromium, molybdenum, tungsten, manganese, rhenium iron, cobalt, nickel, ruthenium, rhodium, palladium, osmium, iridium, platinum, copper, zinc or combinations thereof The second framework metal, $M^1$, is different from the first framework metal, M. When there are more than one $M^1$ atoms, each $M^1$ is bound through an oxygen atom to another $M^1$.

The atoms which are replaced in such substitution include, but are not limited to: molybdenum, tungsten, vanadium or combinations thereof. The number of framework atoms replaced may be from 1 to 3 or more, and the substituting metals, which are different from the replaced metal, may each be the same metal, for example iron, or may be different from each other, for example two or three different metal atoms; e.g., one iron atom may replace one tungsten atom; two iron atoms may replace two tungsten atoms; three iron atoms may replace three tungsten atoms; two atoms, different from each other, for example iron and cobalt, may replace two tungsten atoms; three atoms, different from each other, for example iron, cobalt and nickel, may replace three tungsten atoms; two atoms of iron and one atom of cobalt may replace three tungsten atoms; and so on.

Replacement of three framework atoms of a polyoxometallate salt by three atoms, different from the framework atom, two of which replacing atoms are selected from the group consisting of iron, chromium, manganese or ruthenium, and the third of which is different from the two just referred to and is a transition metal, is disclosed in U.S. Pat. No. 5,091,354 (Lyons et al.).

The polyoxometallate may comprise (1) at least 6 atoms of a first framework metal or metals comprising molybdenum, tungsten, vanadium or combinations thereof and (2) at least one atom of a second framework metal or metals comprising a transition metal other than molybdenum, tungsten or vanadium. When there is more than one second framework metal, they may comprise a combination of the available transition metals.

In one embodiment, the polyoxometallate used in the present invention comprises 9 to 11 atoms of a first framework metal selected from the group consisting of molybdenum, tungsten and vanadium, and 1 to 3 atoms of a second framework metal such as titanium, zirconium, vanadium, niobium, tantalum, chromium, molybdenum, tungsten, manganese, rhenium, iron, cobalt, nickel, ruthenium, rhodium, palladium, osmium, iridium, platinum, copper or zinc, which second metal is a transition metal different from the first framework metal. The second framework metals, $M^1$, are site-specific, regioselective substitutions wherein each $M^1$ is bound through an oxygen atom to another $M^1$.

Typically, the polyoxometallate support component of the catalysts of the present invention may be prepared by adding a soluble salt of the desired cation, for example $Cs_2CO_3$ for a cesium salt support, to the desired soluble heteropolyacid, for example $H_3(PMo_{12}O_{40})$, to form the insoluble polyoxometallate, for example $Cs_3(PMo_{12}O_{40})$. The polyoxometallates may be isolated by any means, such as by filtration or solvent evaporation, and preferably by solvent evaporation. Certain polyoxometallate precipitates may be isolated without need for an evaporation step. However, in many cases the precipitate is very fine and isolation is preferably done by evaporation of water. The desired proportion of the metal oxides may vary somewhat from the theoretical amount required for the desired product.

The salt solution is preferably added slowly into the heteropolyacid solution to precipitate the cation heteropolymetallate salt. The following reaction exemplifies the process:

$$3Cs_2CO_3 + 2H_3(PMo_{12}O_{40}) \rightarrow 2Cs_3(PMo_{12}O_{40}) + 3H_2O + 2CO_2$$

The precipitation may be performed at an elevated temperature (e.g., 60–65° C.) and $CO_2$ is evolved during the reaction. The resulting polyoxometallate salt forms fine suspension in water and may be evaporated to dryness, for example by rotary evaporation, or by heating, such as at 50 to 70 ° C. or below. The dried material may be calcined/heat treated (e.g., at 300° C.).

The method of preparation of the polyoxometallates can influence the surface area, the pore volume and the pore size distribution ("PSD") of the polyoxometallate salts. For example, slow addition of the cation salt to the heteropolyacid solution results in a material with few small pores and many large pores. In contrast, rapid addition of the cation salt yields a broad PSD with many small pores and some intermediate and large pores. For the present invention, slow addition to form mainly large pores is preferable; for example, at a rate of 2 ml/minute, particularly when using solution concentrations of approximately 0.1 mol/L. More preferably, particularly for the preparation of large quantities of material, the solutions of the cation salt and the heteropolyacid may be added simultaneously to a reaction vessel. The salt solution may have a concentration in the range of from about 0.05 to 1 mol/L, preferably 0.1 to 0.2 mol/L. The heteropolyacid solution may have a concentration in the range of from about 0.05 to 1 mol/L, preferably 0.1 to 0.2 mol/L, and more preferably 0.1 mol/L.

A further factor influencing the PSD is the temperature of the reaction medium during the precipitation step. Precipitation at room temperature yielded a narrow PSD with a median pore radius of about 90 Å, whereas precipitation at 65° C. was found to result in a broader PSD with a greater median pore radius ($\geq 120$ Å).

Additionally, it has been found that aging of the slurry containing the polyoxometallate salt, followed by slow evaporation to dryness, is beneficial to the production of large pore materials. Preferably, the slurry is allowed to remain at room temperature or at a temperature in the range from approximately 35° C. to 45° C. for an extended period of time and is then slowly dried. The aging and drying process may extend for a period of 1 to 3 days or longer. Also, the use of excess cation salt (relative to the stoichiometric amount) promotes formation of the desired large-pore support material. While the support material can be prepared using stoichiometric ratios of starting materials, it is preferred to use a slight excess of the cation salt.

The preparation of polyoxometallates with random framework-metal substitution, such as $K_6(SiMo_{11}MnO_{39})$ and $K_5(PW_{11}VO_{40})$, is known. For example, $K_5(PW_{11}VO_{40})$ may be prepared by dissolving 45.0 g of 12-tungstophosphoricacid, $H_3(PMo_{12}O_{40})$, in 105 ml of water. With stirring, the pH is adjusted to about 5.2 with potassium bicarbonate. The mixture is then heated to 70 ° C. and 6.0 g of vanadyl sulfate ($VOSO_4$) in 15 ml water is added. The solution is cooled and potassium chloride is added to precipitate the desired $K_5(PW_{11}VO_{40})$.

The preparation of regiospecific, trilacunary framework-substituted polyoxometallates may also be useful in the present invention. Suitable regiospecific, trilacunary framework-substitutedpolyoxometallates are described in U.S. Pat. No. 4,898,989, herein incorporated by reference to the extent it teaches the preparation of such substituted compounds.

The catalysts useful in the present invention are any which may be supported on apolyoxometallate support. It will be appreciated by those skilled in the art that a wide variety of catalysts may be supported according to the present invention. Suitable catalysts include, but are not limited to: mixed metal oxides, vanadium phosphorus compounds, and combinations thereof. Other suitable catalysts include those used in polymerization reactions, petroleum processing, hydrogenations, ammoxidations, and the like. More than one catalyst of a particular type may be used advantageously in the present invention. For example, more than one mixed metal oxide catalyst may be supported on a polyoxometallate salt. Other catalysts, such as heteropolyacids, may be advantageously combined with the catalysts of the present invention. When the catalyst of the present invention includes a mixed metal oxide, it is preferred that one or more heteropolyacids are used in combination with the mixed metal oxide.

Heteropolyacids useful in combination with the catalysts of the present invention are those of the formula

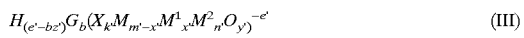  (III)

wherein G is an element selected from Groups 1–16 or an oxy ion thereof; X is an element selected from Groups 3–16; M=molybdenum, tungsten or a combination thereof; $M^1$=vanadium; $M^2$ is a transition metal different from M and $M^1$; z'=the charge on G; b=0 to 12; k'=1 to 5; m'=5 to 20; x'=0 to 6; n'=0 to 3; y'=18 to 62; and e' is the charge of the polyoxometallate anion. Suitable heteropolyacids include, but are not limited to: $H_3PMo_{12}O_{40}$, $H_3PW_{12}O_{40}$, $(VO)_{1.5}PMo_{12}O_{40}$, $(VO)_{1.5}PW_{12}O_{40}$, $(TiO)_{1.5}PMo_{12}O_{40}$, $H(VO)PMo_{12}O_{40}$, $H(VO)PW_{12}O_{40}$, $H_5PV_3Mo_9O_{40}$, $H_5PV_2Mo_{10}O_{40}$, $H_5PV_2W_{10}O_{40}$, $H_4PVW_{11}O_{40}$, $RhPMo_{12}O_{40}$, $BiPMo_{12}O_{40}$, $HCrPVMo_{11}O_{40}$, $HBiPVMo_{11}O_{40}$, or combinations thereof. It is preferred that the heteropolyacid is $H_3PMo_{12}O_{40}$, $H_3PW_{12}O_{40}$, $(VO)_{1.5}PMo_{12}O_{40}$, $H(VO)PMo_{12}O_{40}$, $H_5PV_2Mo_{10}O_{40}$, $H_4PVMo_{12}O_{40}$, $RhPMo_{12}O_{40}$, $HCrPVMo_{11}O_{40}$, or $HBiPVMo_{11}O_{40}$. It is more preferred that the heteropolyacidis $H_3PMo_{12}O_{40}$, $H_3PW_{12}O_{40}$, $(VO)_{1.5}PMo_{12}O_{40}$, $H(VO)PMo_{12}O_{40}$. When the heteropolyacidis, for example, $(VO)_{1.5}PMo_{12}O_{40}$, $(TiO)_{1.5}PMo_{12}O_{40}$, $RhPMo_{12}O_{40}$, or $BiPMo_{12}O_{40}$, the necessary acid typically comes from a separate acid source, such as sulfuric acid in the $VOSO_4$ used to make $(VO)_{1.5}PMo_{12}O_{40}$. Such amount of acid is sufficient for the present invention.

The amount of catalyst supported on the polyoxometallate salts may be any amount that effectively catalyzes the desired reaction. Typically, the amount of the catalyst used in the present invention is that amount sufficient to cover the surface area of the polyoxometallate support, although less may be effectively used. One skilled in the art will appreciate that the amount of catalyst needed will depend on the particular catalyst used, the surface area of the support and the particular reaction to be catalyzed. Any amount of heteropolyacid is suitable for use in combination with the catalysts of the present invention.

Mixed metal oxide catalysts useful in the present invention are those of the formula

  (II)

wherein A is selected from molybdenum, tungsten, iron, niobium, tantalum, zirconium, ruthenium, and mixtures thereof; $M^3$ is selected from vanadium, cerium, chromium, and mixtures thereof; L is selected from tellurium, bismuth, antimony, selenium, and mixtures thereof; Z is selected from niobium, tantalum, tungsten, titanium, aluminum, zirconium, chromium, manganese, iron, ruthenium, cobalt, rhenium, nickel, palladium, platinum, antimony, bismuth, boron, indium, cerium, and mixtures thereof; a'=0.25 to 0.98; m'=0.003 to 0.5; l=0.003 to 0.5; z'=0.003 to 0.5; and o is dependent on the oxidation state of the other elements. It is preferred that a'=0.35 to 0.87; m'=0.045 to 0.37; l=0.02 to 0.27; and z'=0.005 to 0.35. It is preferred that A is selected from molybdenum, tungsten and combinations thereof. It is preferred that $M^3$ is selected from vanadium, cerium, chromium and mixtures thereof. L is preferably selected from tellurium, bismuth, antimony and mixtures thereof. Z is preferably selected from niobium, tantalum, zirconium and mixtures thereof.

In a particularly useful mixed metal oxide, A is selected from molybdenum, tungsten and combinations thereof; $M^3$ is selected from vanadium, cerium, chromium and mixtures thereof; L is preferably selected from tellurium, bismuth, antimony and mixtures thereof; and Z is preferably selected from niobium, tantalum, zirconium and mixtures thereof. It is preferred that A is molybdenum; $M^3$ is vanadium; L is tellurium; and Z is niobium.

The mixed metal oxides useful in the present invention are described in U.S. Pat. No. 5,380,933, herein incorporated by reference to the extent it teaches the preparation of these compounds.

Suitable mixed metal oxide catalysts containing nickel and molybdenum include, but are not limited to: $Ni_{0.45}Co_{0.50}MoO_4$, $Ni_{0.45}CO_{0.45}V_{0.07}MoO_4$, $Ni_{0.45}Co_{0.45}Ce_{0.07}MoO_4$, $Ni_{0.45}Co_{0.45}Bi_{0.03}V_{0.03}MoO_4$, $Ni_{0.45}C0_{0.45}Bi_{0.07}MoO_4$, $Ni_{0.45}CO_{0.45}Sb_{0.03}V_{0.03}MoO_4$, $Ni_{0.45}Co_{0.45}Fe_{0.07}MoO_4$, $Ni_{0.5}Co_{0.5}Cs_{0.002}MoO_4$, $Ni_{0.5}CO_{0.5}K_{0.002}MoO_4$. Such catalysts are described in D. L. Stern, R. K. Grasselli, *J. Catal.*, 167, 550 (1997), herein incorporated by reference to the extent it teaches the preparation of these compounds.

The vanadium phosphorus compounds useful as catalysts in the present invention include, but are not limited to, vanadyl pyrophosphate and vanadyl phosphite. Such catalysts are disclosed in G. Centi, *Catalysts Today*, Elsevier, Amsterdam 1993, vol 16, and Cavani et al., *Chemical Reviews*, 1998, vol. 88, 55, herein incorporated by reference to the extent these references teach the preparation of such vanadium phosphorus compounds.

The catalysts useful in the present invention also include molecular precursors of mixed metal oxides and vanadium phosphorus compounds. For example, the molecular clusters of vanadyl pyrophosphate and vanadyl phosphite disclosed in Herron et al., Molecular Precursors to Vanadyl Pyrophosphate and Vanadyl Phosphite, *Journal of the American Chemical Society*, vol. 119, 7149–7150 (1997), may be used as catalysts in the present invention. Such catalyst precursors may be effectively supported on the polyoxometallate salts in the same manner as the catalysts themselves. When the catalyst is a vanadium phosphorus compound, it is preferred that a molecular cluster precursor is used.

The mixed metal oxide molecular precursors useful in the present invention include heteropolyacids and polyoxometallate salts. Mixed metal oxide catalysts useful in the present invention may be prepared by heating a heteropolyacid or polyoxometallate salt, as described above, at a temperature of at least 600° C. for a period of time sufficient to convert the precursor to the mixed metal oxide. It is preferred that the heteropolyacid or polyoxometallate salt is heated for at least 30 minutes, more preferably at least 60 minutes, and most preferably at least 120 minutes. The length of the heating period is dependent on the temperature used and on the particular heteropolyacid or polyoxometallate salt employed. Any amount of time is sufficient as long as the heteropolyacid or polyoxometallate salt has been converted to the desired mixed metal oxide catalyst.

Mixed metal oxide catalysts may be prepared by heating mixed metal oxide molecular precursors in air or inert atmosphere, and preferably in air. The mixed metal oxide molecular precursors may be supported or unsupported during heating. Suitable supports include, but are not limited to: alumina, zirconia, titania, silicon dioxide, polyoxometallate salts and the like. When a polyoxometallate salt is used as the support, it is preferred that the polyoxometallate support be sufficiently stable at the temperatures used for converting the mixed metal oxide precursor to the mixed metal oxide. It is preferred that the support is not a polyoxometallate salt.

The supported catalysts of the present invention may be prepared by preparing the catalysts and supports separately and then combining them or, alternatively, the catalyst may be prepared in the presence of the polyoxometallate support. It is preferred the catalyst and the support are prepared separately and then combined.

The catalysts and supports of the present invention may be combined by any means, such as wet grinding, dry grinding, wet impregnation, incipient wetness, evaporative coating, or any other method leading to the deposition of the catalyst on the support or a physical mixing of the two. The catalyst may be situated on the polyoxometallate support either before or after heat treating the catalyst. It is preferred that the catalysts and supports are combined by wet coating, evaporative coating, incipient wetness, or wet grinding.

When unsupported, the catalysts used in the present invention are typically heat treated. These catalysts will typically require heat treatment when supported on the polyoxometallate salts of the present invention. However, the heat treatment conditions of polyoxometallate supported catalysts may vary from the heat treatment conditions for the same catalyst when unsupported in order to achieve the desired crystal phase of the catalyst. Such differences in heat treatment conditions will be appreciated by those skilled in the art.

The catalysts of the present invention may be heat treated either before or after being situated on the polyoxometallate support. When the catalyst is a mixed metal oxide, it is preferred that the catalyst is heat treated after being supported on the polyoxometallate.

The catalysts useful in the present invention may be heat treated in atmospheres containing oxygen, such as air, or in inert atmospheres, such as argon, nitrogen and helium. Typically, the catalysts may be heat treated at temperatures up to 650° C. It is preferred that the catalysts of the present invention are heat treated at temperatures up to 600° C. The catalysts of the present invention are typically heat treated for up to 24 hours. It will be appreciated by those skilled in the art that longer heat treatment times may be used as long as the catalyst does not decompose. When higher temperatures, such as greater than about 500° C., are to be used to heat treat a polyoxometallate supported catalyst, it is preferred that the polyoxometallate contains tungsten.

The catalysts of the present invention may be heat treated in any manner. The catalysts of the present invention may be heat treated prior to placing them in a catalytic reactor, heat treated in a catalytic reactor prior to use or heat treated in a catalytic reactor during use. In one embodiment, the supported catalysts of the present invention are placed in a reactor and heat treated without the presence of a reactive gas, such as alkanes. The reactor and catalyst are then cooled. Once cooled, the reactor and catalyst are then heated to a suitable temperature for the desired conversion of the reactive gas and the gas is then fed into the reactor. When the catalysts of the present invention are heat treated during use, the catalysts are placed in a catalytic reactor and a reactive gas is fed into the reactor as the temperature of the reactor is raised to the desired heat treatment temperature. After such heat treatment, the reactor temperature is lowered to a suitable temperature for the desired conversion of the reactive gas and the reaction is continued.

The polyoxometallate supported catalysts of the present invention are useful in catalyzing all reactions where unsupported catalysts and catalysts supported on other supports are useful. For example, the supported catalysts of the present invention are useful in the oxidation of alkanes to alcohols, oxidation of alkanes to unsaturated carboxylic acids, oxidation of alkanes to unsaturated anhydrides, oxidation of alkenes, oxidative dehydrogenation of alkanes to alkenes, oxidation of aromatic hydrocarbons, olefin polymerization, olefin epoxidation, hydrosulfurization processes, and oxidation of alkenes. The polyoxometallate supported catalysts of the present invention are also useful for petroleum processing, polymerization, hydrogenation, ammoxidation, or any process where a supported catalyst is useful. The catalysts of the present invention are preferably used in the oxidation of alkanes to alcohols, oxidation of alkanes to unsaturated carboxylic acids, oxidation of alkanes to unsaturated anhydrides, oxidative dehydrogenation of alkanes to alkenes and oxidation of alkenes.

The catalysts of the present invention are particularly useful in the conversion of alkanes to unsaturated organic compounds. Suitable unsaturated organic compounds include, but are not limited to: unsaturated carboxylic acids, unsaturated aldehydes, unsaturated ketones, unsaturated anhydrides, alkenes and combinations thereof It is preferred that the supported catalysts of the present invention are used in the conversion of alkanes to unsaturated carboxylic acids, alkenes, unsaturated anhydrides and combinations thereof. Suitable alkenes include both substituted alkenes and unsubstituted. By substituted alkenes is meant an alkene having one or more hydrogens replaced with a substituent group, such as cyano. Suitable unsaturated organic compounds include, but are not limited to: acrylic acid, methacrylic acid, maleic acid, acrolein, methacrolein, acrylonitrile, methacrylonitrile,propylene, isobutylene, butylene, butadiene, maleic anhydride, and combinations thereof.

In one embodiment, a catalyst of the present invention having a mixed metal oxide on a polyoxometallate support, is used to convert alkanes to unsaturated carboxylic acids. For example, propane is converted to acrylic acid and isobutane is converted to methacrylic acid. The selectivity of this reaction is increased relative to that catalyzed by the same catalyst that is not supported on a polyoxometallate support.

In one embodiment of the invention, the supported catalysts of the present invention may be pre-treated with water, such as steam. The catalyst is prepared by exposure to air saturated with water vapor or steam for approximately 48 hours. The hydrated catalyst may comprise about 5 to 30 weight percent water. This pretreatment of the catalyst by hydration may enhance catalytic activity.

Other pretreatment methods, such as pretreatment with amines, may be used successfully with the catalysts of the present invention. Suitable amines include pyridine, 2,2'-bipyridine, quinoline, and pyridine N-oxide.

When the compositions of the present invention are used to catalyze alkane oxidations, an alkane is contacted with an oxidizing agent and a heat treated catalyst of the present invention, to yield such products as unsaturated carboxylic acids, unsaturated anhydrides, alkenes, unsaturated anhydrides, unsaturated ketones, and the like.

The alkanes useful in the present invention may be linear, branched, or cyclic and are any which are gaseous at the temperature of the reaction. It is preferred that the alkanes useful in the present invention are gaseous at 370° C., and more preferably gaseous at 225° C. Thus, alkanes having 2 to 20 carbon atoms may be used successfully in the present process. The alkanes maybe single compounds or mixtures of compounds. The purity of the alkanes is not critical, although it is preferable to avoid the presence of compounds which may poison the catalyst. Suitable alkanes include, but are not limited to: ethane, propane, n-butane, iso-butane, n-pentane, iso-pentane, cyclopentane, hexane, cyclohexane, heptane, octane, cyclooctane, decane, dodecane, tetradecane, hexadecane and mixtures thereof As a result, the feedstock for the present process may, in addition to the alkane or alkanes of interest, further comprise methane or ethane as well as impurities such as air or carbon dioxide. In the conversion of alkanes to alkenes, the preferred alkanes have 2 to 12 carbon atoms, and more preferably 2 to 8 carbon atoms. Suitable preferred alkanes useful in the conversion to alkenes include, but are not limited to: ethane, propane, n-butane, iso-butane, pentane, iso-pentane, hexane, iso-hexane, ethylhexane, cyclopentane, cyclohexane and mixtures thereof. Especially preferred alkanes include ethane, propane and isobutane. In the conversion of alkanes to unsaturated carboxylic acids, the preferred alkanes have 3 to 12 carbon atoms, and more preferably 3 to 8 carbon atoms. Suitable preferred alkanes useful in the conversion to unsaturated carboxylic acids include, but are not limited to: propane, n-butane, iso-butane, pentane, iso-pentane, hexane, iso-hexane, ethylhexane, cyclopentane, cyclohexane and mixtures thereof. More preferred alkanes useful in the conversion to unsaturated carboxylic acids include propane and isobutane. Butane is the preferred alkane in the conversion of alkanes to unsaturated anhydrides.

Suitable oxidizing agents, or oxidants, useful in alkane oxidations of the present invention include, but are not limited to: air, oxygen enriched air, molecular oxygen, hydrogen peroxide, nitrogen oxides and mixtures thereof. It is preferred that the oxidizing agent is air, molecular oxygen or nitrogen oxides, and more preferably the oxidizing agent is air. The amount of the oxidizing agent useful in the present invention is any amount sufficient to oxidize the alkane. For example, the amount of oxidizing agent may be any amount up to or greater than the stoichiometric amount, based on the amount of alkane. Furthermore, by controlling the amounts of oxidizing agent and alkane, the catalyst may be kept oxidized or reduced and the lifetime and reactivity of the catalyst may be controlled.

It will be appreciated by those skilled in the art that the alkane oxidations of the present invention may be carried out under a variety of conditions. The conditions necessary are generally those under which the oxidizing agent functions to oxidize the alkane to an unsaturated carboxylic acid, unsaturated anhydride or alkene. Thus, it is preferred that the process of the present invention is run under oxidizing conditions.

The compositions of the present invention may be used as catalysts for reactions carried out in the vapor phase or in solution, and preferably in the vapor phase. In the process of the present invention, an alkane, optionally an inert diluting gas and optionally gaseous promoters and/or modifiers, and an oxidant if the reaction is an oxidation, are fed into a reactor. Suitable inert gases include, but are not limited to: nitrogen, argon, helium or the like. Preferably, the feedstock is an alkane gas. The alkane, oxidant and optional diluting gas may be mixed prior to being fed into the reactor or may be mixed in the reactor.

The reactions catalyzed by the compositions of the present invention may be carried out in the presence or absence of steam. When the reaction is an alkane oxidation, it is preferred that it is carried out in the presence of steam. When an inert, diluting gas is used in the process of the invention, determination of the molar ratio of alkane, oxidant, if present, diluting gas and water (steam), if present, in the starting reaction gas mixture is within the ability of the skilled practitioner in the art. Determination of the gas space velocity used in the process of the invention is within the ability of the skilled practitioner in the art.

The temperature used in the process of the present invention is that which favors the desired reaction products, such as unsaturated carboxylic acids, unsaturated anhydrides or alkenes. Using a method for forming unsaturated carboxylic acids for purposes of exemplification the process of the present invention is carried out at a temperature in the range from 225° C. to 500° C. The process of the invention is typically performed at a temperature of at least about 225° C., and preferably at least about 275° C., and below that which will cause an undesirable level of decomposition of the alkane to carbon oxide and water and/or decomposition of the catalyst. Generally, the temperature is not above 450° C., more preferably not above 400° C. Thus, a preferred temperature range is from 275° C. to 400° C. It will be appreciated that when higher process temperatures are used, such as >400° C., tungsten polyoxometallates are more stable and are therefore preferred for such high temperature processes. The determination of the most desirable temperature for a given reaction and given catalyst within the scope of the invention is within the ability of the person skilled in the art.

The pressure used in the process of the invention is not critical, but is important. For example, the pressure used in the present process may affect the selectivity of alkene formation. The process may be successfully carried out at atmospheric pressure. Other pressures may be used, and the determination of the most desirable pressure for a given reaction within the scope of the invention is within the ability of the person skilled in the art.

The gas phase alkane conversion process of the present invention may be carried out in any suitable reactor configuration. For example, the reaction may be performed in a fixed-bed, moving bed, ebullating bed reactor, or other as is within the ability of the person skilled in the art to determine.

It will be appreciated that unreacted alkane from the process of the present invention may be recycled and passed through the reactor one or more times. Such a recycle has the advantage of increasing the yield of unsaturated organic compound. It will be further appreciated that the process of the present invention may be combined with a process using the unsaturated organic compounds as feedstock, such as processes for the polymerization of unsaturated carboxylic acids or production of unsaturated carboxylic acids, alcohols or the like from alkenes. In such cases, the process of the present invention may be used to produce alkenes, which can then be reacted directly to form such products as unsaturated carboxylic acids, such as acrylic acid or methacrylic acid, or alcohols. In an alternative embodiment, the catalysts of the present invention may be combined with one or more additional catalysts. Such combined catalyst systems have the advantage that conversion of alkanes to unsaturated carboxylic acids or alkenes and then conversion of these products to other reaction products may be performed within one reactor or reactor system.

As the alkanes useful in the alkane conversion process of the present invention increase in carbon chain length, it is preferred that the pore size of the polyoxometallates also increase. For example, when alkanes having more than about 8 carbon atoms are used in the process of the present invention, it is preferred that the polyoxometallate supports have large pores.

Catalysts supported on polyoxometallates containing a majority of large pores are prepared by first preparing polyoxometallates containing large pores and then combining the catalysts with such polyoxometallates. The preparation of such large pore polyoxometallates is described above. However, such preparatory methods do not provide polyoxometallates having exclusively large pores. Rather, such methods provide polyoxometallates having a median pore size that is larger, meaning small pores are still present. The pore sizes of polyoxometallate supports can be controlled by heat treating, that is, polyoxometallate supports having small pores are converted into polyoxometallates having an even greater proportion of large pores.

The pore sizes of polyoxometallate salts alone can be controlled by heat treating, that is, polyoxometallate salts having small pores are converted into polyoxometallate salts having a greater proportion of large pores. Such a method of preparing large pore polyoxometallate salts may have advantages over known methods of preparation. For example, it allows the preparation of polyoxometallates having a wide variety of pore sizes. Such variety of pore sizes provides for maximizing the surface area of the supported catalysts.

FIG. 1 illustrates plot of pore volume versus pore diameter for mixed metal oxide catalysts supported on a cesium polyoxometallate ("CsPOM") having the formula $Cs_3PMo_{12}O_{40}$ and for an unsupported mixed metal oxide catalyst ("mixed oxide"). The supported mixed metal oxides were prepared by wet impregnation ("wet impreg."), dry coating after calcination ("post cal."), and dry coating before calcination ("pre-cal.").

The pore size of the polyoxometallate supports may be controlled by heating the polyoxometallate at a temperature in the range of 38° to 600° C. It is preferred that the pore size is controlled by heating the polyoxometallate at a temperature in the range of 390° to 550° C., and more preferably at a temperature in the range of 410° to 500° C.

The pore size of the polyoxometallate support may be controlled by first heating the polyoxometallate followed by supporting the catalyst on the polyoxometallate. It is preferred that the pore size of the polyoxometallate supports are controlled by heat treating after catalyst preparation, that is, after the catalyst has been supported on the polyoxometallate.

The following examples are presented to illustrate further various aspects of the present invention, but are not intended to limit the scope of the invention in any aspect. All reagents were of good commercial grade and were used without further purification.

EXAMPLE 1

The polyoxometallate supports were prepared according to the following general procedure, illustrated for $Cs_3PMo_{12}O_{40}$. $Cs_3PMo_{12}O_{40}$ was prepared by adding 33.31 g of $Cs_2CO_3$ in 1225 g deionized water to 159.47 g $H_3PMo_{12}O_{40}$ in 800 g deionized water at 50° C. The addition was performed over 2 hours and the mixture was maintained at 50° C. for an additional 30 minutes. After cooling to room temperature, the mixture was stirred slowly for approximately 70 hours. The water was then removed by evaporation and the resulting solid product was dried in a vacuum oven or at elevated temperature (for example 300° C.), yielding approximately 150 g of the desired polyoxometallate support.

Typical polyoxometallates useful in the present invention are reported in Table 1.

TABLE 1

| Polyoxometallate Supports |
| --- |
| $Cs_3PMo_{12}O_{40}$ |
| $Cs_3PW_{12}O_{40}$ |
| $Cs_4PVMo_{11}O_{40}$ |
| $BiPMo_{12}O_{40}$ |

EXAMPLE 2

Six catalyst samples of a mixed metal oxide catalyst, $Mo_{1.00}V_{0.30}Te_{0.23}Nb_{0.08}O_x$, supported on a cesium polyoxometallate, $Cs_3PMo_{12}O_{40}$, were prepared by dry grinding the mixed metal oxide and cesium polyoxometallate together.

Samples 1 to 3 were prepared by combining the mixed metal oxide catalyst precursor, that is the uncalcined solid, and $Cs_3PMo_{12}O_{40}$ in a Spex 8000 mixer/mill along with two 5 mm ziconia beads and grinding for 40 minutes. After grinding, the supported catalysts were calcined under argon by heating at 2° C./min to 200° C. for 1 hour and then at 2° C./min to 600° C. for 2 hours. The amounts of mixed metal oxide and polyoxometallate support used are reported in Table 2.

Samples 4 to 6 were prepared by first calcining the mixed metal oxide under argon by heating at 2° C./min to 200° C. for 1 hour and then at 2° C./min to 600° C. for 2 hours. After calcination, the mixed metal oxide and $CS_3PMo_{12}O_{40}$ along with two 5 mm ziconia beads were placed in a Spex 8000 mixer/mill and ground for 40 minutes. The amounts of mixed metal oxide and polyoxometallate support used ted in Table 2.

The supported catalysts were evaluated for their effectiveness in the conversion of propane to acrylic acid in a microreactor at 380° C. using 1% propane in humidified air with a 3 second contact time. Samples C1–C4 were used as comparatives. Sample C1 contained only the calcined mixed metal oxide catalyst. Sample C2 contained the calcined mixed metal oxide catalyst that had been ground as described above. Sample C3 contained only the polyoxometallate salt that had been ground as described above. Sample C4 contained mixed metal oxide that was first ground, then calcined. The results are also reported in Table 2.

TABLE 2

| Sample | Weight of MMO (g) | Weight of POM (g) | Propane Conversion | AA Selectivity | AA Yield | Surface Area (m²/g) |
| --- | --- | --- | --- | --- | --- | --- |
| 1 | 0.14 | 1 | 3.7 | 10.8 | 0.4 | 7.5 |
| 2 | 0.28 | 1 | 1.4 | 21.4 | 0.3 | 8.2 |
| 3 | 0.42 | 1 | 3.6 | 27.8 | 1.0 | 9.3 |
| 4 | 0.10 | 1 | 7.5 | 16.0 | 1.2 | 41.4 |
| 5 | 0.20 | 1 | 11.1 | 14.4 | 1.6 | 37.8 |
| 6 | 0.40 | 1 | 10.8 | 17.6 | 1.9 | 34.7 |
| C1* | — | — | 25.1 | 36.0 | 9.0 | 4.4 |
| C2* | — | — | 49.4 | 22.9 | 11.3 | 5.1 |
| C3* | — | — | 5.3 | 5.7 | 0.3 | 49.1 |
| C4* | — | — | 26.2 | 6.5 | 1.7 | 3.8 |

*Control

The above data show that mixed metal oxide catalysts can be successfully supported on polyoxometallate salts.

EXAMPLE 3

Three catalyst samples of a mixed metal oxide catalyst, $Mo_{1.00}V_{0.30}Te_{0.23}Nb_{0.08}O_x$, supported on a cesium polyoxometallate, $Cs_3PMo_{12}O_{40}$, were prepared by wet impregnating the cesium polyoxometallate with the mixed metal oxide. Each sample was prepared by having the cesium polyoxometallate present in the reaction vessel during the preparation of the mixed metal oxide. After preparation of the supported catalyst, the samples were calcined according to the procedure described in Example 2. The amounts of the mixed metal oxide catalyst and cesium polyoxometallate used are reported in Table 3.

The supported catalysts were evaluated for their effectiveness in the conversion of propane to acrylic acid in a microreactor under the conditions as described in Example 2. Samples C5 and C6 were used as comparatives. Sample C5 contained only the mixed metal oxide precursor that had been calcined after grinding, as described above. Sample C6 contained the calcined mixed metal oxide catalyst. The results are also reported in Table 3.

TABLE 3

| Sample | Weight of MMO (g) | Weight of POM (g) | Propane Conversion (%) | AA Selectivity (%) | AA Yield (%) | Surface Area (m²/g) |
| --- | --- | --- | --- | --- | --- | --- |
| 7 | 0.14 | 1 | 3.7 | 13.5 | 0.5 | 12.7 |
| 8 | 0.28 | 1 | 9.2 | 19.6 | 1.8 | 12.3 |
| 9 | 0.42 | 1 | 6.3 | 38.1 | 2.4 | 10.3 |
| C5* | — | — | 26.2 | 6.5 | 1.7 | 3.8 |
| C6* | — | — | 19.7 | 26.9 | 5.3 | 6.2 |

*Control

The above clearly show that mixed metal oxide catalysts can be successfully supported on polyoxometallate salts.

EXAMPLE 4

Five samples containing a mixture of a mixed metal oxide catalyst and a heteropolyacid ("HPA") catalyst supported on a cesium polyoxometallate were prepared. Each sample contained either 0.14 g or 0.42 g of $Mo_{1.00}V_{0.30}Te_{0.23}Nb_{0.08}O_x$ as the mixed metal oxide catalyst and 1 g of $Cs_3PMo_{12}O_{40}$ as the polyoxometallate support. Sample 10 was prepared by dry grinding the polyoxometallate with calcined mixed metal oxide catalyst as described in Example 2, followed by dry grinding with 20 mol % phosphomolybdic acid as the HPA. Sample 11 was prepared by dry grinding the polyoxometallate with calcined mixed metal oxide catalyst as described in Example 1, followed by wet impregnating with 20 mol % phosphomolybdic acid. Sample 12 was prepared by dry grinding the polyoxometallate with mixed metal oxide catalyst precursor, that is uncalcined, as described in Example 2, followed by calcining the mixture and then dry grinding with with 20 mol % phosphomolybdic acid. Sample 13 was prepared by wet impregnating the polyoxometallate with mixed metal oxide catalyst precursor, followed by calcining the mixture and then dry grinding with 20 mol % phosphomolybdic acid. Sample 14 was prepared by wet impregnating the polyoxometallate with mixed metal oxide catalyst precursor, followed by calcining the mixture and then wet impregnating with 20 mol % phosphomolybdic acid.

Samples 10–14 were evaluated for their effectiveness in the conversion of propane to acrylic acid in a microreactor, under the conditions as described in Example 2. All of the samples had selectivities under 10%. The results are reported in Table 4.

TABLE 4

| Sample | Propane Conversion (%) | AA Selectivity (%) | AA Yield (%) |
|---|---|---|---|
| 10 | 19.2 | 7.8 | 1.5 |
| 11 | 34 | 5 | 1.7 |
| 12 | 15 | 10 | 1.5 |
| 13 | 13.9 | 13 | 1.8 |
| 14 | 51.2 | 5.1 | 2.6 |

EXAMPLE 5

A polyoxometallate supported vanadium phosphorus catalyst was prepared by first preparing the molecular cluster precursor of $(VO)_2P_2O_7$, as described in Herron et al. Molecular Precursors to Vanadyl Pyrophosphate and Vanadyl Phosphite, *Journal of the American Chemical Society*, vol. 119, 7149–7150 (1997), taking the precursor up in methanol and coating a polyoxometallate of the formula $Cs_3PMo_{12}O_{40}$. The resulting slurry was then dried and heated to 300° C., and then placed in a microreactor to evaluate its effectiveness in the conversion of propane to acrylic acid in a microreactor, using 1% propane in humidified air with a 3 second contact time. The catalyst was first heated to 380° C. in the microreactor, followed by heat treatment at 420° C. for 3 hours and then cooling to 380° C. The percent of propane conversion, AA yield and propylene yield were measured before heat treatment and after each hour of heat treatment. The results are reported in Table 5.

TABLE 5

| Temperature | Propane Conversion (%) | AA Yield (%) | Propylene Yield (%) |
|---|---|---|---|
| 380° C. | 5.7 | 0 | 0 |
| 420° C. - 1 hour | 9.1 | 0.4 | 0 |
| 420° C. - 2 hours | 8.1 | 2.1 | 0.4 |
| 420° C. - 3 hours | 8.1 | 2.3 | 0.4 |

From the above data it can be seen that the vanadium phosphorus catalyst was successfully supported on a polyoxometallate salt.

What is claimed is:

1. A catalyst composition comprising a catalyst situated on a polyoxometallate support; wherein the polyoxometallate support has the formula $$Q_aH_{(e-az)}(X_kM_{m-x}M^1_xM^2_nO_y)^{-e} \quad (I)$$

wherein Q, is a cation selected from potassium, rubidium, cesium, magnesium, calcium, strontium, barium, transition metal, actinide metal, lanthanide metal, metal oxy ion, ammonium, tetraalkylammonium, pyridinium, quinolinium, protonated aromatic amines, protonated aliphatic amines or mixtures thereof X is an element selected from Groups 3–16 elements; M=molybdenum, tungsten or a combination thereof; $M_1$=vanadium; $M_2$ is a transition metal different from M and $M^1$; z=the charge on Q; a is the number of cations Q; k=1 to 5; m=5 to 20; n=0 to 3, x=0 to 6; y=18 to 62; and e is the charge of the polyoxometallate ion; and provided that the catalyst is not a heteropolyacid.

2. The composition of claim 1 wherein the catalyst is selected from the group comprising mixed metal oxides, vanadium phosphorus compounds and mixtures thereof.

3. The composition of claim 2 wherein the mixed metal oxide has the formula $$A_{a'}M^3_{m'}L_{l'}Z_{z'}O_o \quad (II)$$

wherein A is selected from molybdenum, tungsten, iron, niobium, tantalum, zirconium, ruthenium, and mixtures thereof; $M^3$ is selected from vanadium, cerium, chromium, and mixtures thereof; L is selected from tellurium, bismuth, antimony, selenium, and mixtures thereof; Z is selected from niobium, tantalum, tungsten, titanium, aluminum, zirconium, chromium, manganese, iron, ruthenium, cobalt, rhenium, nickel, palladium, platinum, antimony, bismuth, boron, indium, cerium, and mixtures thereof; a'=0.25 to 0.98; m'=0.003 to 0.5; l=0.003 to 0.5; z'=0.003 to 0.5; and o is dependent on the oxidation state of the other elements.

4. The composition of claim 3 further comprising a heteropolyacid.

5. The composition of claim 2 wherein the vanadium phosphorus compound comprises vanadyl phosphite or vanadyl pyrophosphite.

6. The composition of claim 2 wherein the catalyst is present as a molecular precursor.

7. The composition of claim 1 wherein the polyoxometallate support comprises $Cs_3(PMo_{12}O_{40})$, $Cs_4(PMo_{11}VO_{40})$, $Cs_5(PMo_{10}VO_2O_{40})$, $Cs_6(PMo_9V_3O_{40})$, $Cs_3(PW_{12}O_{40})$, $Cs_4(PW_{11}VO_{40})$, $Cs_5(PW_{10}V_2O_{40})$, $Cs_6(PW_9V_3O_{40})$ or combinations thereof.

8. A process for preparing a catalyst composition comprising a catalyst situated on a polyoxometallate support; wherein the polyoxometallate support has the formula $$Q_aH_{(e-az)}(X_kM_{m-x}M^1_xM^2_nO_y)^{-e} \quad (I)$$

wherein Q, is a cation selected from potassium, rubidium, cesium, magnesium, calcium, strontium, barium, transition metal, actinide metal, lanthanide metal, metal oxy ion, ammonium, tetraalkylammonium, pyridinium, quinolinium, protonated aromatic amines, protonated aliphatic amines or mixtures thereof; X is an element selected from Groups 3–16 elements; M=molybdenum, tungsten or a combination thereof; $M^1$=vanadium; $M^2$ is a transition metal different from M and $M^1$; z=the charge on Q; a is the number of cations Q; k=1 to 5; m=5 to 20; n=0 to 3; x=0 to 6; y=18 to 62; and e is the charge of the polyoxometallate ion; including the step of admixing the catalyst with the polyoxometallate support;

provided that the catalyst is not a heteropolyacid.

9. The process of claim 8 wherein the catalyst is selected from the group comprising mixed metal oxides, vanadium phosphorus compounds and mixtures thereof.

10. The process of claim 9 wherein the vanadium phosphorus compound comprises vanadyl phosphite or vanadyl pyrophosphite.

11. The process of claim 9 wherein the catalyst is present as a molecular precursor.

12. The process of claim 8 wherein the mixed metal oxide has the formula $$A_{a'}M^3_{m'}L_{l}Z_{z'}O_{o} \tag{I}$$

wherein A is selected from molybdenum, tungsten, iron, niobium, tantalum, zirconium, ruthenium, and mixtures thereof, $M^3$ is selected from vanadium, cerium, chromium, and mixtures thereof; L is selected from tellurium, bismuth, antimony, selenium, and mixtures thereof, Z is selected from niobium, tantalum, tungsten, titanium, aluminum, zirconium, chromium, manganese, iron, ruthenium, cobalt, rhenium, nickel, palladium, platinum, antimony, bismuth, boron, indium, cerium, and mixtures thereof; a'=0.25 to 0.98; m'=0.003 to 0.5; l=0.003 to 0.5; z'=0.003 to 0.5; and o is dependent on the oxidation state of the other elements.

13. The process of claim 12 further comprising a heteropolyacid.

* * * * *